(12) United States Patent
Watanabe et al.

(10) Patent No.: US 9,823,208 B2
(45) Date of Patent: Nov. 21, 2017

(54) METHOD FOR MEASURING SPREADING RESISTANCE AND SPREADING RESISTANCE MICROSCOPE

(71) Applicant: Hitachi High-Tech Science Corporation, Minato-ku, Tokyo (JP)

(72) Inventors: Masafumi Watanabe, Tokyo (JP); Takehiro Yamaoka, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 59 days.

(21) Appl. No.: 15/084,976

(22) Filed: Mar. 30, 2016

(65) Prior Publication Data

US 2016/0290945 A1 Oct. 6, 2016

(30) Foreign Application Priority Data

Mar. 30, 2015 (JP) .................. 2015-069143

(51) Int. Cl.
| | | |
|---|---|---|
| *G01R 31/26* | (2014.01) | |
| *G01N 27/04* | (2006.01) | |
| *G01N 27/02* | (2006.01) | |
| *G01N 17/00* | (2006.01) | |
| *G01Q 60/30* | (2010.01) | |
| *G01L 1/10* | (2006.01) | |
| *G01L 1/22* | (2006.01) | |
| *G01L 1/20* | (2006.01) | |

(52) U.S. Cl.
CPC .......... *G01N 27/041* (2013.01); *G01N 17/00* (2013.01); *G01N 27/02* (2013.01); *G01Q 60/30* (2013.01); *G01L 1/10* (2013.01); *G01L 1/20* (2013.01); *G01L 1/22* (2013.01)

(58) Field of Classification Search
CPC ........ G01N 17/00; G01N 27/02; G01N 27/04; G01N 35/00; G01L 1/10; G01L 1/20; G01L 1/22; G01R 27/00
USPC .......... 324/76.11–76.83, 439, 459, 500, 549, 324/600, 649, 691, 719, 762.01
See application file for complete search history.

(56) References Cited

U.S. PATENT DOCUMENTS

| 7,373,806 B2 | 5/2008 | Kitajima et al. |
| 2005/0050947 A1 | 3/2005 | Kitajima et al. |

(Continued)

FOREIGN PATENT DOCUMENTS

| JP | 2005-069851 A | 3/2005 |
| JP | 2008-002952 A | 1/2008 |

*Primary Examiner* — Giovanni Astacio-Oquendo
*Assistant Examiner* — Raul Rios Russo
(74) *Attorney, Agent, or Firm* — Banner & Witcoff, Ltd.

(57) ABSTRACT

A method includes: removing at least a part of an oxide formed on a surface of the sample by relatively scanning the surface of the sample in X and Y directions parallel to the surface while bringing a probe into contact with the surface of the sample; detecting a signal by bringing the probe into contact with the surface of the sample from which at least a part of the oxide is removed at a predetermined detection position in the X direction or the Y direction while a bias voltage is applied to the sample; calculating a spreading resistance value based on the signal; and retracting the probe to keep the probe relatively away from the surface in a Z direction perpendicular to the surface while relatively moving the probe to a next detection position to start scanning the sample from the next detection position.

6 Claims, 3 Drawing Sheets

(56) References Cited

U.S. PATENT DOCUMENTS

| | | | | |
|---|---|---|---|---|
| 2005/0212529 A1* | 9/2005 | Huang | ................... | G01Q 20/04 |
| | | | | 324/633 |
| 2006/0207317 A1* | 9/2006 | Watanabe | .............. | B82Y 35/00 |
| | | | | 73/105 |
| 2009/0140142 A1* | 6/2009 | Murayama | ............. | B82Y 35/00 |
| | | | | 250/307 |

* cited by examiner

METHOD FOR MEASURING SPREADING RESISTANCE AND SPREADING RESISTANCE MICROSCOPE

CROSS-REFERENCE TO RELATED APPLICATION

This application claims priority from Japanese Patent Application No. 2015-069143, filed on Mar. 30, 2015, the entire subject matter of which is incorporated herein by reference.

BACKGROUND

1. Field of the Invention

The present disclosure relates to a method for measuring spreading resistance by measuring a two-dimensional spreading current distribution of a sample using a scanning probe microscope and to a spreading resistance microscope.

2. Description of the Related Art

Recently, a scanning spreading resistance microscope (SSRM) has been developed in which a two-dimensional resistance distribution is obtained using a scanning probe microscope by bringing a conductive probe into contact with a surface of a sample, applying a bias voltage thereto, and measuring a current flowing through the probe using a wide range logarithmic amplifier (see, for example, JP-A-2008-002952).

In the SSRM, by scanning a surface of a sample with a probe with a voltage applied between the surface of the sample and the probe and detecting height information of the surface of the sample and a current flowing through the probe, a concave-convex shape of the sample and two-dimensional spreading resistance just below the probe can be acquired at the same time. When a bias voltage is applied to the sample, only carriers positioned in the vicinity just below the probe flow into the probe, and a current flows and local resistance which is obtained by converting the voltage and the current into a resistance value is referred to as spreading resistance. In this way, since the applied voltage is concentrated on just below the probe in the SSRM, a current (spreading resistance) with which a dopant concentration is dominant just below the probe can be detected, this technique is anticipated as being capable of measuring a dopant concentration distribution of semiconductor.

Figure 5:
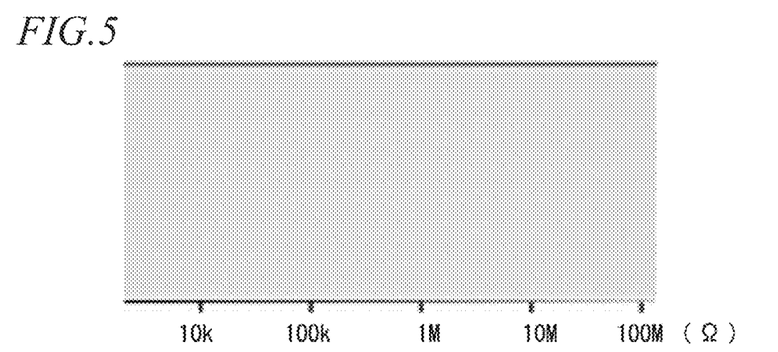
FIG. 5 is a view illustrating a spreading resistance distribution of a Si wafer surface, where the spreading resistance is actually measured using a method for measuring spreading resistance according to the related art.

Incidentally, similarly to an atomic force microscope (AFM), the SSRM glidingly scans the sample surface while bringing the probe into contact with the surface, and sequentially detects a current (resistance) when the probe reaches a predetermined detection position on an XY plane of the sample. However, since the current is measured while continuously changing the position at which the probe is in contact with the sample, as illustrated in FIG. 5, the current value is not stable due to unstable contact resistance of a contact. Therefore, in order to stabilize the contact resistance, current measurement may also be performed by pressing the probe with a predetermined load.

Figure 6:
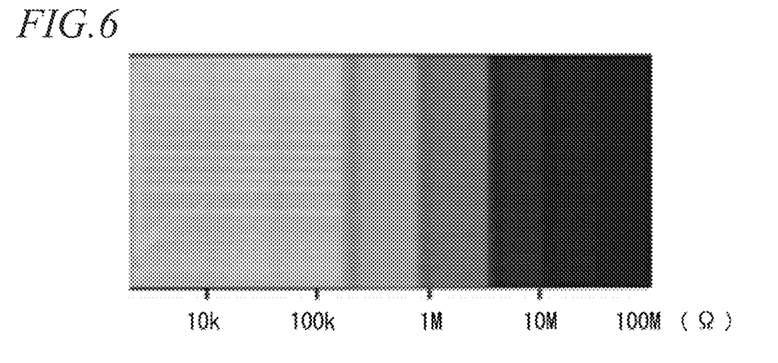
FIG. 6 is another view illustrating a spreading resistance distribution of a Si wafer surface, where the spreading resistance is actually measured using a method for measuring spreading resistance according to the related art.

When measuring spreading resistance of the sample, unintended oxide may be formed on the surface of the sample. For example, when spreading resistance of a Si wafer is measured under atmospheric gas, the sample surface is oxidized to form an oxide during placing the wafer in the SSRM or during measurement. When a current is measured by pressing the probe on the sample with an oxide formed on the surface thereof, the probe strips the oxide into fragments and drags the fragments as they are. For this reason, as illustrated in FIG. 6, sometimes stripe-shaped measurement noise occurs in an image of a spreading resistance distribution.

The wafer of which the surface is oxidized is once removed from the SSRM and the oxide is removed under hydrofluoric acid treatment, mechanical polishing, or the like, and then measurement is performed again. However, measurement efficiency decreases due to replacement of the sample or the sample surface is sometimes oxidized again between oxide removal and measurement.

In the SSRM according to the related art, since current is measured while moving the probe, an average resistance value of a large area including a measurement point in addition to the measurement point representing a detection position is acquired. For this reason, similarly, there may be a problem that measurement noises occur or accurate spreading resistance cannot be obtained due to the dragging of fragments.

SUMMARY

The present disclosure has been made in view of the above-described circumstances, and one of objects of the present disclosure is to provide a method for measuring spreading resistance and a spreading resistance microscope with improved measurement accuracy and high measurement efficiency by suppressing noises while measuring spreading resistance of the sample of which the surface is oxidized.

According to an exemplary embodiment of the present disclosure, there is provided a method for measuring spreading resistance of a sample, the method including: removing at least a part of an oxide formed on a surface of the sample by relatively scanning the surface of the sample in X and Y directions parallel to the surface while bringing a probe into contact with the surface of the sample; detecting a signal by bringing the probe into contact with the surface of the sample from which at least a part of the oxide is removed at a predetermined detection position in the X direction or the Y direction while a bias voltage is applied to the sample; calculating a spreading resistance value based on the signal: and retracting the probe to keep the probe relatively away from the surface in a Z direction perpendicular to the surface while relatively moving the probe to a next detection position to start scanning the sample from the next detection position.

According to another exemplary embodiment of the present disclosure, there is provided a spreading resistance microscope including: a probe that has an electrical conductivity; a controller configured to control relative movement of the probe in X and Y directions parallel to a surface of a sample and relative movement of the probe in a Z direction perpendicular to the surface of the sample; a bias voltage applying unit configured to apply a bias voltage to the sample: a detector configured to detect a signal generated from the probe when the probe is brought into contact with the surface of the sample and the bias voltage is applied to the sample; and a spreading resistance value calculator configured to calculate a spreading resistance value based on the detected signal, wherein the controller operates to perform a process including: removing at least a part of an oxide formed on a surface of the sample by relatively scanning the surface of the sample in X and Y directions parallel to the surface while bringing a probe into contact with the surface of the sample: controlling the detector to detect the signal by bringing the probe into contact with the surface of the sample from which at least a part of the oxide is removed at a predetermined detection position in the X direction or the Y direction while the bias voltage is applied to the sample; and retracting the probe to keep the probe relatively away from the surface in a Z direction perpendicular to the surface while relatively moving the probe to a next detection position to start scanning the sample from the next detection position.

According to the method and the spreading resistance microscope, in a sample on which an unintended oxide affecting the measurement is formed, (i) the oxide is removed to clean the surface of the sample in the oxide removing step and then (ii) the signal detecting step is performed. As a result, unstable measurement of spreading resistance is suppressed and measurement noise is also suppressed because the spreading resistance is not measured while removing the oxide. In the (ii) signal detecting step, since the spreading resistance is measured at the detection position or the probe is kept away from the surface of the sample at a position other than the detection position, a resistance value can be acquired and the spreading resistance can be accurately measured. Similarly, measurement noise generated from the dragging of fragments can be suppressed.

Since the oxide is removed while a sample is placed on the spreading resistance microscope and the spreading resistance can be measured immediately thereafter, it is possible to suppress a decrease in measurement efficiency due to replacement of a sample or to suppress a problem that the surface of the sample is oxidized again between the removal of the oxide and the measurement.

In the signal detecting step, it is preferable that the probe is fixed at the detection position in the X and Y directions.

According to the method and the spreading resistance microscope for measuring spreading resistance, the spreading resistance is measured while fixing the probe to the detection position in the X and Y directions, and thus measurement accuracy is further improved.

When the signal is detected in the signal detecting step, it is preferable that irradiation with light for detecting a position of the probe in the Z direction is stopped.

For example, when the sample is a semiconductor and is irradiated with light in detecting a signal, sometimes resistivity of the surface varies due to photo-excitation. Therefore, the spreading resistance can be more accurately measured by stopping irradiation with light for detecting a position of the probe in the Z direction in detecting a signal.

DETAILED DESCRIPTION

Hereinafter, an embodiment of the present disclosure will be described with reference to the accompanying drawings.

Figure 1A:
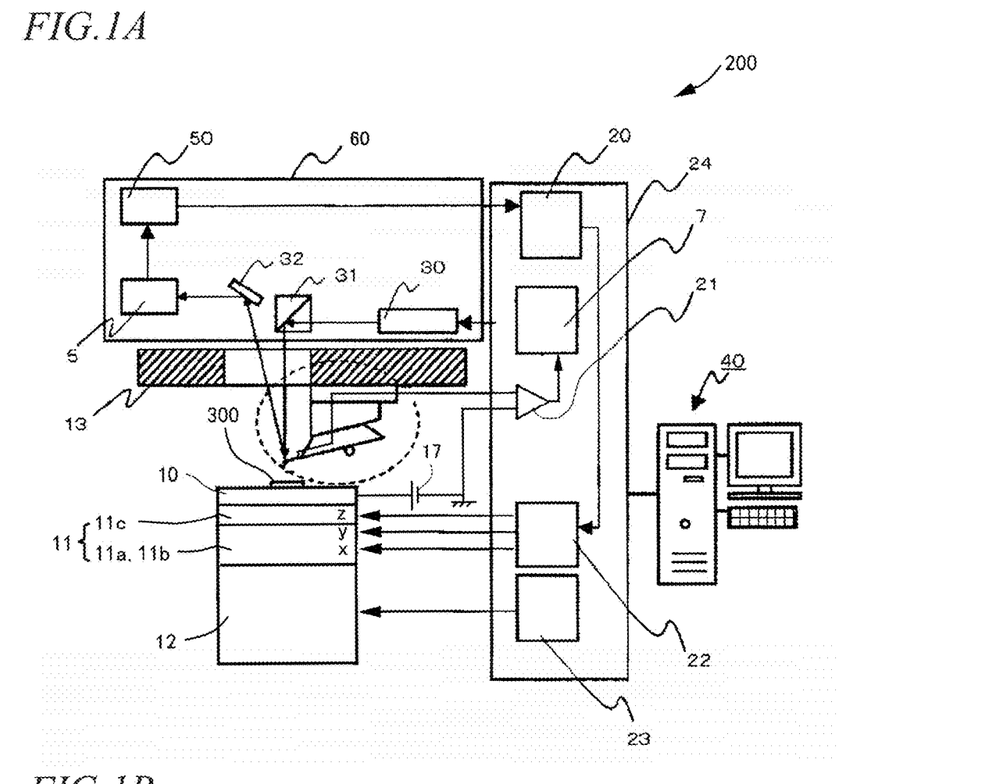
FIGS. 1A and 1B are block diagrams of a spreading resistance microscope.
Figure 1B:
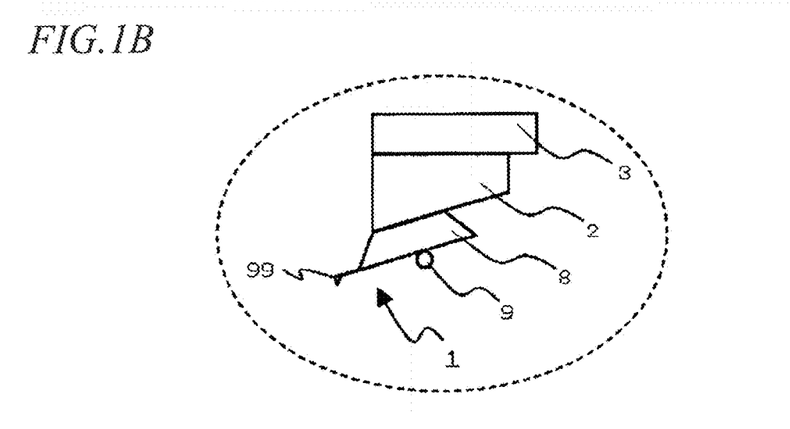

FIGS. 1A and 1B are block diagrams of a scanning spreading resistance microscope (SSRM) 200 to which the present disclosure is suitably applied. FIG. 1A is a diagram illustrating the entire configuration of the scanning spreading resistance microscope 200, and FIG. 1B is a partially enlarged view of the vicinity of a cantilever 1.

As shown in FIG. 1A, the scanning spreading resistance microscope 200 includes the cantilever 1 having a probe 99 at the tip thereof, an actuator (scanner) 11 three-dimensionally scanning (slightly moving) a sample 300, a bias power supply 17, a displacement detector 60 detecting a displacement of the cantilever 1, a controller 24, and a computer 40.

A cylindrical actuator 11 is mounted on an upper side of a coarse adjustment mechanism 12, and a stage 10 is connected to an upper side of the actuator 11. A sample 300 can be placed on the stage 10.

The controller 24 has a Z control circuit 20 to be described later, an XYZ output amplifier 22 controlling the actuator 11, a coarse adjustment control circuit 23 controlling the coarse adjustment mechanism 12, a wide range logarithmic amplifier 21, an computation unit 7 calculating a spreading resistance value from an output value of the logarithmic amplifier 21. The controller 24 is connected to the computer 40, thereby enabling high-speed communication of data. The controller 24 is configured by a micro-computer and the like.

The computer 40 controls an operation condition of circuits in the controller 24, retrieves and controls measured data, and implements surface shape measurement, spreading resistance measurement, or the like. The computer 40 has a control substrate controlling an operation of the scanning spreading resistance microscope 200, a central processing unit (CPU), a ROM, a RAM, a storage unit such as a hard disk, an interface, and an operating unit.

The coarse adjustment mechanism 12 moves the actuator 11 and the stage 10 disposed thereon in roughly three-dimensions and is controlled by the coarse adjustment control circuit 23.

The actuator 11 moves (slightly moves) the stage 10 (and the sample 300) three-dimensionally, and has a cylinder shape including two (biaxial) piezoelectric elements 11a and 11b moving the stage 10 in the X and Y directions (a plane of the sample 300) and the piezoelectric element 11c moving the stage 10 in a Z (height) direction. A piezoelectric element is an element in which crystals are deformed when an electric field is applied thereto or an electric field is generated when the crystals are deformed with an external force. A lead zirconate titanate (PZT) that is a kind of ceramic can be generally used as the piezoelectric element, but the piezoelectric element is not limited thereto.

The piezoelectric elements 11a to 11c are connected to the XYZ output amplifier 22 and a predetermined control signal (voltage) is output to the XYZ output amplifier 22 to drive the piezoelectric elements 11a and 11b in the X and Y directions and to drive the piezoelectric element 11c in the Z direction.

The sample 300 is placed on the stage 10 and the sample 300 is disposed to face the probe 99.

The cantilever 1 comes in contact with a side surface of the cantilever tip 8 and has a cantilever spring structure. The cantilever tip 8 is pressed to a slope block 2 by a cantilever tip presser 9, and the slope block 2 is fixed to a case 13 of the scanning spreading resistance microscope 200.

The back surface of the cantilever 1 is irradiated with a laser beam from a laser beam source 30, and the laser beam reflected by the cantilever 1 is incident on a dichroic mirror 31. The laser beam is further reflected by a mirror 32 and then is detected by a displacement detector 5. The amount of upward or downward (Z direction) movement of the cantilever 1 is reflected in a variation in optical path (incident position) of a laser beam incident on the dichroic mirror 31. Therefore, a displacement of the cantilever 1 is detected from the incident position by the displacement detector 5. The electrical signal of the displacement detector 5 is amplified by the preamplifier 50 and is input to the Z control circuit 20.

A displacement detection unit includes the laser beam source 30, the dichroic mirror 31, the mirror 32, the displacement detector 5, and the preamplifier 50.

In order to maintain the cantilever 1 at a constant amount (amount of deflection) of upward or downward (Z direction)) movement, the Z control circuit 20 transmits a control signal to a Z signal portion of the XYZ output amplifier 22 and the Z signal portion outputs a feedback control signal (voltage) for driving the piezoelectric element 11b in the Z direction. Displacement (deflection) of the cantilever 1 corresponding to force acting between the sample 300) and the probe 99 is detected by the above-described mechanism and the actuator 11c is displaced to maintain this force at a target value, and thus contact force between the probe 99 and the sample 300 is controlled. In this state, the actuators 11a and 11b are displaced in the X and Y directions by the XYZ output amplifier 22 so as to scan the sample 300 and map the shape or physical property of the surface.

As described above, in the present disclosure, measurement is made in a contact mode in which the probe 99 comes in contact with the sample 300 by a predetermined force. In this embodiment, the scanning spreading resistance microscope 200 is set to be operated in a sample scanning manner in which measurement is made by scanning the stage 10 on which the sample 300 is placed.

Regarding the displacement of the stage 10 on the XY plane, (i) a three-dimensional shape image from a height displacement of the stage 10 and (ii) a resistance value into which a current when the following bias voltage is applied between the probe 99 and the sample 300 is converted are displayed on the computer 40 and are subjected to analysis or process, thereby enabling the scanning spreading resistance microscope to operate as a probe microscope.

The bias power supply 17 is connected to the stage 10 and applies a bias voltage to the sample 300 on the stage 10. As described above, when the probe 99 comes in contact with the surface of the sample 300 in the contact mode, a detection signal (current signal in this embodiment) is input from the probe 99 to the logarithmic amplifier 21 constituting a current-voltage amplifier. An output voltage of the logarithmic amplifier 21 is output to the computation unit 7, and the computation unit 7 calculates a spreading resistance value from the voltage output.

The bias power supply 17, the logarithmic amplifier 21, and the computation unit 7 correspond to the "bias voltage applying unit", the "detector", and the "spreading resistance value calculator" respectively. The XYZ output amplifier 22, the controller 24, and the computer 40 correspond to the "controller."

Next, a method for measuring spreading resistance according to an embodiment of the present disclosure will be described. In the embodiment, a sample with an unintended oxide formed on the surface thereof is used as a target for spreading resistance measurement. As described above, for example, this oxide is formed by oxidization of the surface of the sample during placement of the sample on the scanning spreading resistance microscope 200 or during measurement. When the sample is placed on the scanning spreading resistance microscope 200 after an oxide is removed from a sample of which the surface is oxidized or during measurement, sometimes the surface of the sample is oxidized again to form an oxide.

The method for measuring spreading resistance according the embodiment of the present disclosure includes (i) an oxide removing step of relatively scanning the sample in the XY direction parallel to the surface while bringing the probe 99 into contact with the surface of the sample 30X) and removing at least a portion of an oxide formed on the surface, and (ii) a signal detecting step of detecting the signal by bringing the probe 99 into contact with the surface at a predetermined detection position in an X direction or a Y direction with respect to the sample 300 from which at least a portion of the oxide is removed, and then relatively keeping away the probe 99 from the surface in a Z direction perpendicular to the surface while allowing the probe to relatively scan the sample until the probe reaches a next detection position in the X or the Y direction.

Based on the detected signal, a spreading resistance value is calculated as described below.

First, the oxide removing step will be described. In this step, three-dimensional shape of the surface of the sample 300 is measured in the contact mode described above. At this time, a force F1 which is a force for pressing the probe 99 to the sample 300 is set to match the hardness of an oxide (insulting film or the like) formed on the surface of the sample 300 and scanning is performed by breaking and peeling off the insulating film on the surface of the sample 300, and thus (at least a portion of) the insulating film can be removed. It is preferable that the press force F1 is set in the range of several 10 nN to several 10 μN.

A material with which Si or the like is coated on the hard material such as a conductive diamond, or a cantilever in which a tip of a diamond crystal having a sharp shape is used as the probe 99 can be suitably used as the probe 99.

To be exact, the force F1 and a force F2 described below represent a pressing load on the probe 99 with the tip radius of curvature ranging from several tens to several hundreds of nm, and the F1 and the F2 may have the same force.

The F1 is applied to remove the oxide film, and the F2 is added to increase a contact area at the time of spreading resistance measurement.

Next, the signal detecting step will be described. The signal detection, in the above-mentioned contact mode, is performed by pressing the probe 99 on the surface of the sample 300, from which the oxide is removed, to bring the probe 99 into contact with the surface of the sample 300. At this time, since a bias voltage is applied from the bias power supply 17 to the sample 300, carriers contained in the sample 300 just below the probe 99 are in contact with the probe 99, thereby flowing as a signal (current). Therefore, this signal is amplified by the logarithmic amplifier 21 and is calculated as a spreading resistance value by the computation unit 7. Here, the bias voltage steeply decreases just below the probe 99, and only carriers existing in the vicinity of just below the probe 99 are in contact with the probe 99 and the current flows, and thus local resistance (spreading resistance) can be detected.

It is preferable that the force F2, which is a force for pressing the probe 99 at the time of spreading resistance measurement in the contact mode, be in the range of several 10 nN to several 10 μN, similarly to the F1. In this case, the F2 is applied to reliably bring the probe 99 into contact with the surface of the sample 300, to stably perform the current measurement.

However, as described above, in the SSRM of the related art, scanning is performed while bringing the probe into contact with the surface of the sample and spreading resistance is successively measured. Accordingly, there is a problem that measurement noises occur due to dragging of the fragment or accurate spreading resistance cannot be obtained due to an unstable current value caused by unstable contact resistance of a contact.

Figure 2:
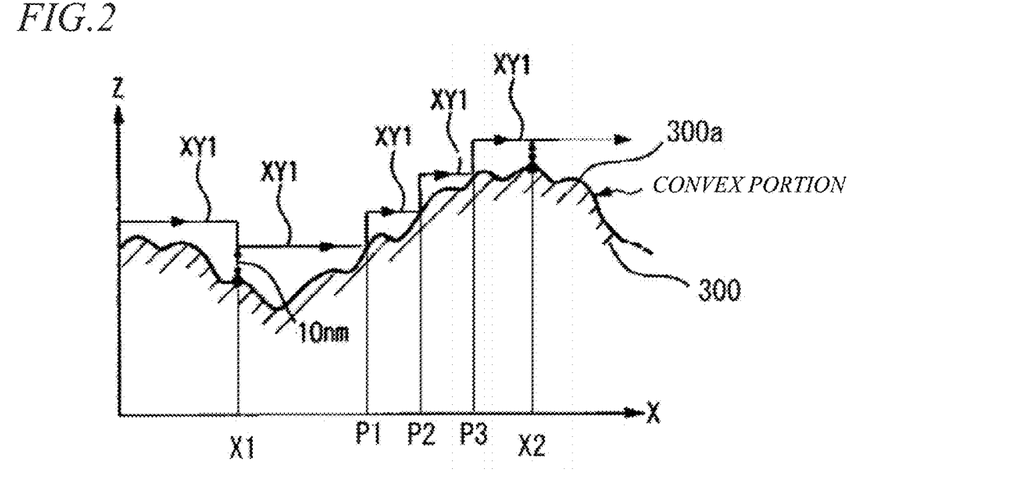
FIG. 2 is a view illustrating a scanning trajectory with a probe for describing a method for measuring spreading resistance according to an embodiment of the present disclosure.

As shown in FIG. 2, in this embodiment, a signal is detected (spreading resistance is measured) by bringing the probe 99 into contact with the sample 300 at a predetermined detection position X1 of the surface (X or Y direction) of the sample 300, and then the probe 99 is kept away from the surface of the sample 300 in a Z direction while allowing the probe 99 to scan the sample until the probe 99 reaches a next detection position X2 in the X direction or the Y direction.

FIG. 2 illustrates only displacements of the X direction (left or right direction on the paper) and the Z direction and does not illustrate displacement of the Y direction.

Specifically, in FIG. 2, first, when the probe 99 scans the sample and reaches a predetermined first detection position X1, the computer 40 controls the XYZ output amplifier 22 to stop scanning in the XY direction and moves the probe 99 in the Z direction approaching the surface of the sample 300a. Here, since the measurement is made in the above-mentioned contact mode, the cantilever 1 is displaced (bent) in response to a force acting between the sample 300 and the probe 99. Therefore, the Z control circuit 20 displaces the actuator 11c to maintain this force at a target value and thus controls a contact force between the probe 99 and the sample 300. The Z control circuit 20 notifies the computer 40 that this force has a target value. When receiving this force, the computer 40 controls the XYZ output amplifier 22 to stop movement in the Z direction. In this state, the computer 40 measures spreading resistance while applying the above-mentioned force F2 between the surface 300a of the sample 300 and the probe 99.

After the spreading resistance at the detection position X1 is measured, the computer 40 controls the XYZ output amplifier 22 to move the probe 99, for example, by 10 nm, in the Z direction in which the probe 99 is kept away from the surface of the sample 300a By raising up the probe 99 by 10 nm, the probe 99 is still trapped in an adsorption water layer which is present at the surface of the sample 300a, the probe 99 can be reliably raised upward from the adsorption water layer. The amount that the probe 99 is raised is not limited to 10 nm.

After raising up the probe 99, the computer 40 controls the XYZ output amplifier 22 to stop a movement in the Z direction, and allows the probe 99 to scan the sample again in the XY direction as an XY trajectory XY1.

Here, since the measurement is made in the above-mentioned contact mode, when the probe 99 approaches a convex portion of the surface 300a of the sample 300, the cantilever 1 is displaced (bent) in response to a force acting between the sample 300 and the probe 99. Therefore, the Z control circuit 20 compares this force with a predetermined value (which is preferable to have a value equal to the above-mentioned target value at the time of the contact, but is not limited thereto), and notifies the computer 40 when this force becomes the predetermined value. In FIG. 2, when the force becomes the predetermined value, a position of the surface 300a of the sample 300 is represented as P1.

When receiving the notification, the computer 40 controls the XYZ output amplifier 22 to stop scanning in the XY direction for a while and moves the probe 99 from the surface of the sample 300a in the Z direction in which the probe is raised up away by the amount described above. After movement in the Z direction, the computer 40 stops movement in the Z direction and performs scanning by the probe 99 again in the XY direction.

In the course of the scanning in this way, when convex portions P1, P2, and P3 of the sample 300 are present in a scanning path, the computer 40 controls the XYZ output amplifier 22 and allows the probe 99 to scan the sample up to the next detection position X2 by repeating operations such as a stop of a scanning for a while, raising up, and scanning again. When the probe 99 reaches the detection position X2, spreading resistance is measured in the same manner as described above. Spreading resistance distribution of the surface of the sample 300 can be obtained by repeating the above-mentioned scanning, spreading resistance measurement, and raising up the probe 99 in sequence and measuring spreading resistance at all the detection positions.

As described above, in the method for measuring spreading resistance according to this embodiment, since in (i) the oxide removing step, an oxide which affects the measurement and is formed on the surface of the sample is removed to clean the surface of the sample and then (ii) the signal detecting step is performed, unstable measurement of the spreading resistance is suppressed and the measurement noise is suppressed without measuring the spreading resistance while removing the oxide. In (ii) the signal detecting step, since the spreading resistance is measured at the detection position and the probe 99 is kept away from the surface of the sample 300 in the position other than the detection position, a resistance value of a measurement point representing the detection position can be acquired. As a result, it is possible to accurately measure the spreading resistance and suppress occurrence of measurement noise due to dragging of fragments.

In particular, when the probe 99 is fixed at the detection position in the XY direction, more stable current value is measured and thus the spreading resistance can be more accurately measured. In this case, it is preferable that the relative position of the probe and the sample be fixed by 1 msec or less in a state in which the probe 99 is pressed.

In the method for measuring spreading resistance according to this embodiment, since the oxide is removed while a sample 300 is placed on the spreading resistance microscope and the spreading resistance can be measured immediately thereafter, it is possible to suppress decrease of measurement efficiency due to replacement of a sample or to suppress a problem that the surface of the sample is oxidized again between the removal of the oxide to the measurement.

Raising up the probe 99 described above with reference to FIG. 2 is similar to an operation of a scanning probe microscope disclosed in the JP-A-2005-069851, but this scanning probe microscope keeps the probe 99 away from the surface of the sample 300 in the position other than the detection position and thus the oxide of the surface of the sample cannot be removed by the probe 99 in this state.

When a signal is detected in (ii) the signal detecting step, it is preferable that the computer 40 control the laser beam source 30 to stop irradiation with light (laser beam) for detecting the position of the probe 99 in the Z direction. For example, when the sample is a semiconductor and is irradiated with light in detecting a signal. sometimes resistivity of the surface varies due to photo-excitation. Therefore, the spreading resistance can be more accurately measured by stopping irradiation with light when a signal is detected.

Figure 3:
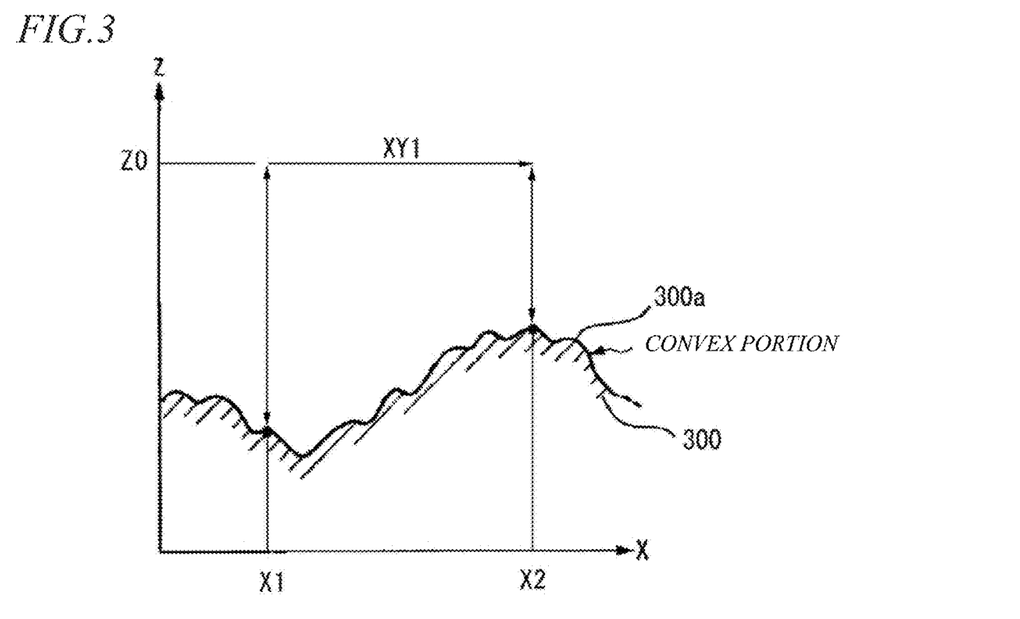
FIG. 3 is a view illustrating another example of the scanning trajectory of the probe.

In (ii) the signal detecting step, the method of keeping the probe 99 away from the surface of the sample 300 at a position other than the detection position is not limited to FIG. 2. For example, as illustrated in FIG. 3, the probe 99 may be uniformly raised up to a predetermined initial height Z0 in the Z direction at a position other than the detection positions X1 and X2. For example, the initial height Z0 may be a height when a voltage is not applied to the actuator 11*c* and the actuator 11*c* has shrunk to the initial position, but is not limited thereto as long as the probe can be sufficiently spaced from the convex portion of the sample 300.

However, in the method illustrated in FIG. 2, the surface of the sample 300 is scanned in the shortest path along the shape of the convex portion while avoiding the convex portion of the surface of the sample. Accordingly, the method illustrated in FIG. 2 is preferable from the viewpoint of reduction in the scanning time, that is, reduction in the measurement time.

Figure 4:
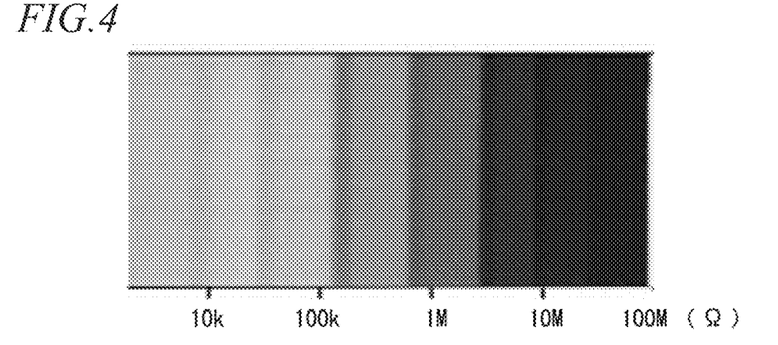
FIG. 4 is a view illustrating a distribution of spreading resistance of a Si wafer surface, the spreading resistance being actually measured by using the method for measuring spreading resistance according to this embodiment.

FIGS. 4 to 6 illustrate distributions of the spreading resistance of the sample surface. The sample is a Si wafer doped with p-type dopant, and the concentration of the p-type dopant is changed stepwise from the left to the right in the drawing. B-doped diamond is used as the probe 99 and the bias voltage is set to +0.5 V. The sample is left in atmospheric gas for about three weeks to form an oxide on the surface thereof.

FIG. 4 illustrates a measurement result using the method for measuring spreading resistance according to this embodiment. Since the oxide on the sample surface is removed and then the spreading resistance is measured in a state in which the probe is raised at a position other than the detection position, there is no measurement noise and a resistance value gradually changing from the left to the right in the drawing depending on the concentration of the p-type dopant is accurately reproduced.

Meanwhile, in FIG. 5, since the spreading resistance is measured without removing the oxide on the sample surface and without applying the force F2 in addition, the contact resistance of the contact is unstable and the gradually changing resistance value cannot be clearly measured.

In FIG. 6, since the spreading resistance is measured with the addition of applying the force F2 but without removing the oxide on the sample surface, a stripe-shaped measurement noise extending horizontally (in the scanning direction) is generated in the spreading resistance distribution image. This is considered to be because the probe strips the oxide to form oxide fragments and drags the oxide fragments as it is.

In the present disclosure, a computer program for measuring the spreading resistance is realized by appropriately storing the process flow performed by the computer 40 as a computer program in a storage unit of the computer 40, and is executed by the controller 24 and the CPU in the computer 40.

The present disclosure is not limited to the above-mentioned embodiment.

For example, the present disclosure can also be applied to a cantilever scanning system for performing measurement by scanning the cantilever side of the scanning probe microscope.

According to the present disclosure, it is possible to improve measurement accuracy and measurement efficiency by suppressing measurement noise of spreading resistance of a sample with an oxide formed on the surface thereof.

What is claimed is:

1. A method for measuring spreading resistance of a sample, the method comprising:
   removing at least a part of an oxide formed on a surface of the sample by relatively scanning the surface of the sample in X and Y directions parallel to the surface while bringing a probe into contact with the surface of the sample;
   detecting a signal by bringing the probe into contact with the surface of the sample from which at least a part of the oxide is removed at a predetermined detection position in the X direction or the Y direction while a bias voltage is applied to the sample;
   calculating a spreading resistance value based on the signal; and
   retracting the probe to keep the probe relatively away from the surface in a Z direction perpendicular to the surface while relatively moving the probe to a next detection position to start scanning the sample from the next detection position.

2. The method according to claim 1,
   wherein, in detecting the signal, the probe is fixed at the predetermined detection position in the X and Y directions.

3. The method according to claim 1,
   wherein, in detecting the signal, light irradiation for detecting a position of the probe in the Z direction is stopped.

4. A spreading resistance microscope comprising:
   a probe that has an electrical conductivity;
   a controller configured to control relative movement of the probe in X and Y directions parallel to a surface of a sample and relative movement of the probe in a Z direction perpendicular to the surface of the sample;
   a bias voltage applying unit comprising a bias power supply and configured to apply a bias voltage to the sample;
   a detector configured to detect a signal generated from the probe when the probe is brought into contact with the surface of the sample and the bias voltage is applied to the sample; and
   a spreading resistance value calculator configured to calculate a spreading resistance value based on the detected signal,
   wherein the controller operates to perform a process including:
   removing at least a part of an oxide formed on the surface of the sample by relatively scanning the surface of the sample in X and Y directions parallel to the surface of the sample while bringing a probe into contact with the surface of the sample;
   controlling the detector to detect the signal by bringing the probe into contact with the surface of the sample from which at least a part of the oxide is removed at a predetermined detection position in the X direction or the Y direction while the bias voltage is applied to the sample; and
   retracting the probe to keep the probe relatively away from the surface of the sample in a Z direction perpendicular to the surface of the sample while relatively moving the probe to a next detection position to start scanning the sample from the next detection position.

5. The spreading resistance microscope according to claim 4, wherein the controller controls the probe to be fixed at the predetermined detection position in the X and Y directions.

6. The spreading resistance microscope according to claim 4,
wherein the controller stops light irradiation for detecting a position of the probe in the Z direction when detecting the signal.

\* \* \* \* \*